(12) United States Patent
McCarty

(10) Patent No.: US 11,786,461 B2
(45) Date of Patent: Oct. 17, 2023

(54) NALOXONE FORMULATIONS FOR SUBLINGUAL AND/OR BUCCAL ADMINISTRATION

(71) Applicant: Pharmaceutical Productions, Inc., Miami Springs, FL (US)

(72) Inventor: John A. McCarty, Miami Springs, FL (US)

(73) Assignee: Pharmaceutical Productions, Inc., Miami Springs, FL (US)

(*) Notice: Subject to any disclaimer, the term of this patent is extended or adjusted under 35 U.S.C. 154(b) by 237 days.

(21) Appl. No.: 17/395,614

(22) Filed: Aug. 6, 2021

(65) Prior Publication Data

US 2022/0016026 A1 Jan. 20, 2022

Related U.S. Application Data

(62) Division of application No. 16/797,205, filed on Feb. 21, 2020, now Pat. No. 11,129,795.

(60) Provisional application No. 62/808,363, filed on Feb. 21, 2019, provisional application No. 62/808,386, filed on Feb. 21, 2019.

(51) Int. Cl.
*A61K 9/06* (2006.01)
*A61K 9/00* (2006.01)
*A61K 31/4355* (2006.01)

(52) U.S. Cl.
CPC ............... *A61K 9/06* (2013.01); *A61K 9/006* (2013.01); *A61K 31/4355* (2013.01)

(58) Field of Classification Search
CPC ....... A61K 9/06; A61K 9/006; A61K 31/4355
See application file for complete search history.

(56) References Cited

U.S. PATENT DOCUMENTS

| | | |
|---|---|---|
| 2017/0340620 A1 | 11/2017 | Shan et al. |
| 2018/0092839 A1 | 4/2018 | Gooberman |
| 2018/0147143 A1 | 5/2018 | Amancha et al. |
| 2018/0153795 A1 | 6/2018 | Amancha et al. |

FOREIGN PATENT DOCUMENTS

| | | |
|---|---|---|
| WO | 90/04965 A1 | 5/1990 |
| WO | 2007041544 A1 | 4/2007 |
| WO | 2016/007245 A1 | 1/2016 |
| WO | 2018/034920 A1 | 2/2018 |
| WO | 2018/148382 A1 | 8/2018 |
| WO | 2019/064026 A1 | 4/2019 |

*Primary Examiner* — Shirley V Gembeh
(74) *Attorney, Agent, or Firm* — Honigman LLP; Andrew S. Chipouras

(57) ABSTRACT

Liquid, gel, and semi-solid compositions containing naloxone base, or isomers or derivatives thereof, with one or more non-aqueous solvents, and optional viscosity adjusting agents, are provided. Methods of treating an individual exhibiting symptoms of respiratory depression associated with known or suspected opioid overdose including administering a liquid, gel, or semi-solid formulation containing a solution of naloxone base, or an isomer or a derivative thereof, in one or more non-aqueous solvents, are also provided.

7 Claims, 1 Drawing Sheet

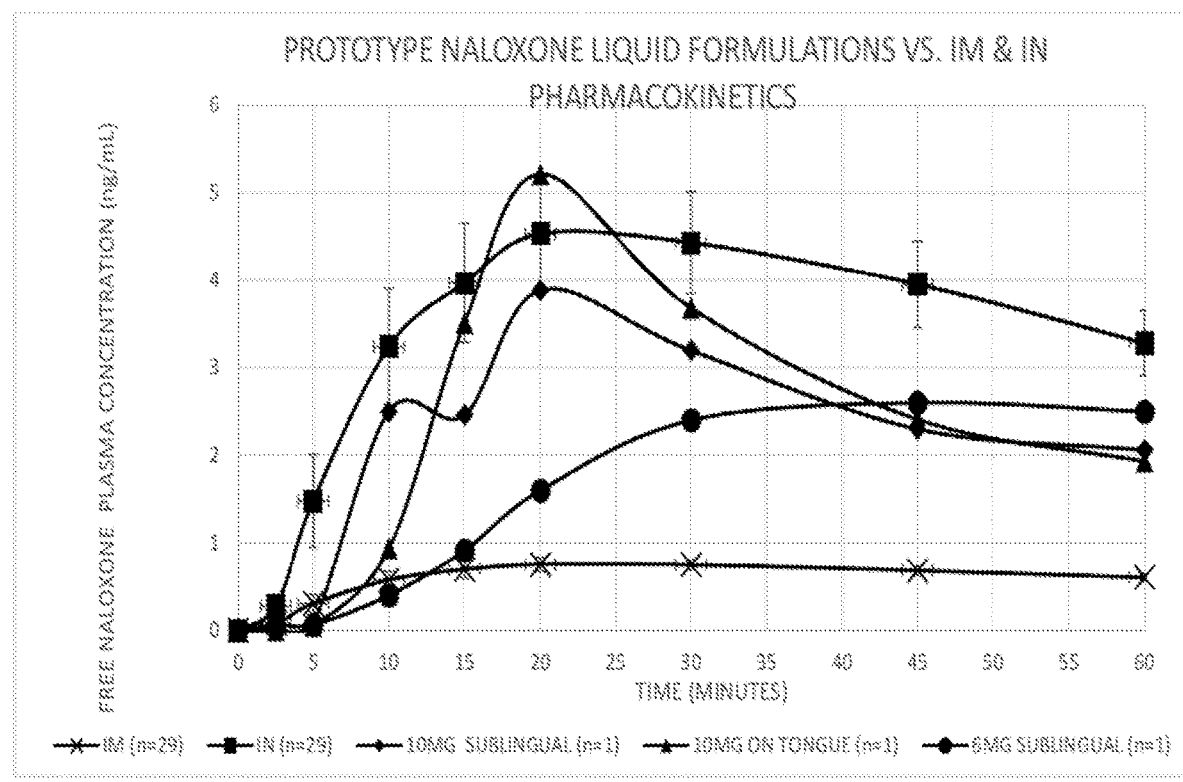

NALOXONE FORMULATIONS FOR SUBLINGUAL AND/OR BUCCAL ADMINISTRATION

CROSS-REFERENCE TO RELATED APPLICATIONS

The present application is a divisional of U.S. Ser. No. 16/797,205 filed Feb. 21, 2020, which claims priority to United States Provisional Application No. 62/808,363, filed on Feb. 21, 2019, and United States Provisional Application No. 62/808,386, filed on Feb. 21, 2019, both of which are incorporated by reference herein in their entireties.

FIELD OF THE INVENTION

The invention is directed to liquid, gel, or semi-solid compositions containing naloxone base, or isomers or derivatives thereof, with one or more non-aqueous solvents. The invention is further directed to methods of treating respiratory depression associated with known or suspected opioid overdoses.

BACKGROUND OF THE INVENTION

An opioid overdose is toxicity due to excessive opioids. Symptoms include, but are not limited to, insufficient breathing, small pupils, and unconsciousness. Among individuals who initially survive an opioid overdose, medical complications can include, but are not limited to, rhabdomyolysis, pulmonary edema, compartment syndrome, and permanent brain damage. See, e.g., E. W. Boyer, *Management of opioid analgesic overdose*, 367 NEW ENGLAND J. MEDICINE 146 (2012), incorporated by reference herein in its entirety. Risk factors for opioid overdose include, but are not limited to, opioid dependence, injecting opioids, using high doses of opioids, mental disorders, and use of opioids together with alcohol, benzodiazepines, or cocaine. See, e.g., T. W. Park, *Understanding Risk Factors for Opioid Overdose in Clinical Populations to Inform Treatment and Policy*, 10 J. ADDICTION MEDICINE 369 (2016), incorporated by reference herein in its entirety. Opioid use disorders resulted in 122,000 deaths globally in 2015, up from 18,000 deaths in 1990. See, e.g., GBD 2015 Mortality and Causes of Death Collaborators, *Global, regional, and national life expectancy, all-cause mortality, and cause-specific mortality for 249 causes of death, 1980-2015: a systematic analysis for the Global Burden of Disease Study 2015*, 388 LANCET 1459 (2016), incorporated by reference herein in its entirety. Further, the rate of opioid overdoses has tripled since 2000 and more deaths were reported in the United States in 2017 than in any previous year on record. In 2017, opioid overdose deaths accounted for 47,600 deaths in the United States. See, e.g., Lawrence Scholl, et al., *Drug and Opioid-Involved Overdose Deaths—United States, 2013-2017*, 67 MORBIDITY & MORTALITY WEEKLY REPORT 1419 (2019), incorporated by reference herein in its entirety.

Initial treatment of an individual exhibiting symptoms of opioid overdose involves supporting the individual's breathing and providing oxygen. See, e.g., A. R. de Caen, et al., *Part 12: Pediatric Advanced Life Support:* 2015 *American Heart Association Guidelines Update for Cardiopulmonary Resuscitation and Emergency Cardiovascular Care*, 18 (Suppl. 2) CIRCULATION S526 (2015), incorporated by reference herein in its entirety. Naloxone is then recommended among those who are not breathing in order to reverse the opioid effects. Among individuals who refuse to go to a hospital following reversal, the risks of a poor outcome in the short term appear to be low. See, e.g., R. Chou, et al., *Management of Suspected Opioid Overdose With Naloxone in Out-of-Hospital Settings: A Systematic Review*, 167 ANNALS OF INTERNAL MEDICINE 867 (2017), incorporated by reference herein in its entirety.

Naloxone, also known as N-allylnoroxymorphone or 17-allyl-4,5α-epoxy-3,14-dihydroxymorphinan-6-one, is a lipophilic compound that acts as a non-selective and competitive opioid receptor antagonist. Naloxone is a synthetic morphinan derivative derived from oxymorphone. Naloxone is highly lipophilic, which allows naloxone to rapidly penetrate the brain and to achieve a higher brain-to-serum ratio than that of morphine. See, e.g., Reginald Dean, et al., *Opiate Receptors and Antagonists: From Bench to Clinic*, SPRINGER SCI. & BUSINESS MEDIA 514 (2009), incorporated by reference herein in its entirety. Naloxone base has the following structure:

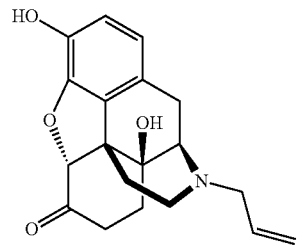

Naloxone hydrochloride is currently available at many pharmacies as (Narcan®) a spray formulation for intranasal (IN) administration and as an intramuscular injection (IM) using an autoinjector (Evzio®). However, the high cost per dosage unit of Narcan® and Evzio® relegates use mainly to first responders, i.e., police or EMT personnel. Typically, the IN and IM are administered by first responders arriving at the scene, the time for which can vary from 5 to 15 minutes and up to 30 minutes after an individual suffering from opioid overdose has been found unconscious and emergency services have been contacted. Consequentially, an individual exhibiting symptoms of respiratory depression associated with known or suspected opioid overdose may live or die simply depending upon when the first-responders reach the individual's physical location.

Further, given the expense of the currently marketed naloxone dosage forms, naloxone can be a budget buster for municipalities, making availability a problem even among first responders. A more affluent municipality may supply Narcan® IN to first responders, while a less affluent, adjacent municipality may not have sufficient revenue to supply Narcan® IN to first responders. Thus, there is a long-felt need for a lower cost alternative, which can be more widely available.

Narcan® IN became the first FDA approved non-injectable naloxone product for the treatment of opioid overdose. EMS programs have now moved toward intranasal administration of naloxone to avoid needle stick risks because many patients needing naloxone are injection drug users and 80% of this patient population in large metropolitan areas is Hepatitis C or HIV positive.

Narcan® IN is supplied in 2 mg or 4 mg dosage strength metered sprays of 0.1 milliliter volume. The current Narcan® IN formulation includes inactive ingredients including benzalkonium chloride (preservative), disodium ethylenediaminetetraacetate (stabilizer), sodium chloride, hydrochloric acid to adjust pH, and purified water. The pH range for Narcan® IN is 3.5 to 5.5. Such a pH range of 3.5 to 5.5 is highly acidic and may irritate the nasal mucosa. Further, because Narcan® is available in nasal spray dispenser form, the formulation may drip out of the nasal cavity resulting in the dosage being swallowed and not available for treating respiratory arrest.

Further, in many circumstances intranasal administration may not be suitable for persons unresponsive due to opioid overdose. Examples include cases involving damage to, or obstruction of, the nasal mucosa or cavity from habitual snorting of cocaine, opioids, or other substances of abuse. In a study by Barton et al., it was shown that 9 out of 52 subjects (17%) who received intranasal naloxone for suspected opioid overdose were unresponsive to the treatment. See, e.g., Erik D. Barton, et al., *Efficacy of intranasal naloxone as a needleless alternative for treatment of opioid overdose in the prehospital setting*, 29 J. EMERGENCY MEDICINE 265 (2005), incorporated by reference herein in its entirety. Five (56%) of the nine non-responders had epistaxis (n=2), nasal mucus (n=1), trauma (n=1), or septal abnormality (n=1), while none of the intranasal naloxone responders had any nasal abnormalities. In addition, excess mucus production and changes in mucociliary clearance rates may also affect bioavailability. During a common cold or sinus congestion, the efficacy of intranasal medication is frequently compromised. Accordingly, a route of administration aside from intramuscular and intranasal is an unmet need for out-of-hospital management of opioid overdose. Accordingly, there remains an unmet need in opioid overdose therapy. If new, safe, less expensive and effective liquid, gel, or semi-solid formulations of naloxone for sublingual and/or buccal administration could be developed, this would represent a useful contribution to the art. Further, if new methods could be found of treating known or suspected opioid overdoses by administering sublingually and/or buccally a liquid, gel, or semi-solid formulation containing naloxone, this would also represent a useful contribution to the art and save thousands of lives.

SUMMARY OF THE INVENTION

In an embodiment, the present disclosure provides a liquid, gel or semi-solid pharmaceutical comprising from about 1% to about 25% of naloxone base, or a derivative thereof, by the total mass of the composition; and from about 50% to about 99% of one or more non-aqueous solvents selected from the group consisting of oleic acid, liquid polyethylene glycol, propylene glycol, and ethanol, or mixtures thereof, by the total mass of the composition; wherein the naloxone base, or derivative thereof, is completely and homogeneously dissolved in the one or more non-aqueous solvents. In some embodiments, the composition further comprises from about 1% to about 25% of a viscosity adjusting agent, by the total mass of the composition.

In another embodiment, the present disclosure provides pharmaceutical compositions comprising: naloxone base, or an isomer or a derivative thereof, in an amount of from about 1 mg to about 20 mg; and one or more non-aqueous solvents selected from the group consisting of oleic acid, liquid polyethylene glycol, propylene glycol, and ethanol, or mixtures thereof, in a combined amount of from about 50 mg to about 500 mg; wherein the naloxone base, or isomer or derivative thereof, is completely and homogeneously dissolved in the one or more selected non-aqueous solvents.

For clarification, naloxone base is completed dissolved in this non-aqueous solvent system or vehicle to form a true single-phase solution. As such, this vehicle composition does not include emulsifiers or surfactants, which would result in two-phase systems such as an emulsion, dispersion, or liquid crystalline systems or precursors to such systems, e.g., self-emulsifying drug delivery systems.

In another embodiment, the present disclosure provides pharmaceutical compositions for sublingual or buccal delivery further comprising one or more viscosity adjusting agents selected from the group consisting of calcium silicate, acacia, carbomers, carboxymethylcellulose sodium, silicon dioxide, hydroxyethyl cellulose, hydroxyethylmethyl cellulose, hydroxypropyl cellulose, hypromellose, methylcellulose, polyvinylpyrrolidone, polyvinyl alcohol, polyethylene glycols or mixtures thereof, in a combined amount of from about 1 mg to about 125 mg.

In yet another embodiment, the present disclosure provides pharmaceutical compositions for sublingual or buccal delivery, wherein the pharmaceutical compositions contain a concentration of naloxone base, or an isomer or a derivative thereof, in the one or more non-aqueous solvents, of from about 1% to about 25%, as a percentage of mass of the naloxone base, or isomer or derivative thereof, in the combined mass of the one or more non-aqueous solvents.

In yet another embodiment, the present disclosure provides pharmaceutical compositions for sublingual or buccal delivery, wherein the pharmaceutical composition provides a plasma concentration of naloxone of at least about 1 ng/mL within about 10 minutes following sublingual or buccal administration of the pharmaceutical composition to an individual.

In yet another embodiment, the present disclosure provides pharmaceutical compositions for sublingual or buccal delivery to an individual, wherein the individual is exhibiting symptoms of respiratory depression associated with known or suspected opioid overdose.

In yet another embodiment, the present disclosure provides pharmaceutical compositions configured to be administered sublingually or buccally to an individual from a single unit dosage form container selected from the group consisting of a spray dispenser, an oral syringe, or a blow-fill-seal unit dose dispenser.

In yet another embodiment, the present disclosure provides methods for treating an individual exhibiting symptoms of respiratory depression associated with known or suspected opioid overdose that can include the steps of: (a) providing a single unit dosage form including a solution of naloxone base, or a derivative thereof, as a completely, homogeneously dissolved solute in one or more non-aqueous solvents; and (b) administering the single unit dosage form sublingually or buccally to the individual.

In yet another embodiment, the present disclosure provides methods for treating an individual exhibiting symptoms of respiratory depression associated with known or suspected opioid overdose, wherein the single unit dosage form further includes one or more viscosity adjusting agents.

In yet another embodiment, the present disclosure provides methods for treating an individual exhibiting symptoms of respiratory depression associated with known or suspected opioid overdose, further including the step of: (c) repeating step (b) if the individual does not recover from respiratory depression within about 2 to 5 minutes following the administering of step (b).

In yet another embodiment, the present disclosure provides methods for treating an individual exhibiting symptoms of respiratory depression associated with known or suspected opioid overdose, wherein the plasma concentration of naloxone in the individual is at least about 1 ng/mL within about 15 minutes (e.g., within about 10 minutes) following the administering step (b).

BRIEF DESCRIPTION OF THE DRAWINGS

FIG. 1 depicts the free naloxone plasma concentration over time following administration of naloxone compositions prepared according to an embodiment of the present invention as compared to intramuscular ("IM") and intranasal ("IN") administration of commercially available formulations of naloxone.

DETAILED DESCRIPTION

The present invention provides naloxone compositions and methods of treatment of opiate overdose induced respiratory depression. In certain embodiments, the present invention provides pharmaceutical formulations for rapid transmucosal delivery of naloxone base, e.g., for sublingual or buccal administration at or near physiological pH.

Transmucosal delivery includes, but is not necessarily limited to, the oral, tongue, esophagus, and nasal mucosa. Buccal administration is a topical route of administration by which a drug held or applied in the buccal area (i.e., in the oral cavity, between the gum and the cheek of an individual) permeates through the oral mucosa and enters directly into the bloodstream. Sublingual administration is a transmucosal route of administration by which a drug product is placed under the tongue of an individual and permeates through the oral mucosa and enters directly into the bloodstream.

The physiological pH values of the various transmucosal membranes vary considerably. The physiological pH of the gastrointestinal tract increases along its length from about pH 1 in the stomach to about pH 8 in the colon. Saliva has a pH of about 6.8. The pH of nasal fluids ranges from about 5.5 to about 6.5. Without being bound by theory, the present invention is designed to provide rapid transmucosal absorption of naloxone base in the pH range specific to the target mucosal tissue, which avoids local irritation. Accordingly, transmucosal absorption of liquid, gel, and semi-solid formulations of naloxone base, according to embodiments of the present invention, occurs independently of local pH as naloxone base is insoluble in water and therefore cannot change the pH of saliva or mucosal tissue. Without being bound by theory, transmucosal delivery of liquid, gel, and semi-solid formulations of naloxone base, according to embodiments of the present invention, requires only the development of a hydration or dielectric gradient from water in the saliva. This results in the formation of a supersaturated naloxone solution as water from saliva interacts with the non-aqueous drug vehicle, which increases the driving force for transmucosal drug absorption.

Naloxone hydrochloride is not natively amenable to sublingual delivery even though it is soluble in water. This is supported by the low naloxone plasma levels obtained from Suboxone®, a combination buprenorphine/naloxone hydrochloride sublingual tablet (SLT). Naloxone's mean absolute bioavailability from Suboxone® SLT is approximately 3%. Mean peak naloxone plasma levels (Cmax) averaged 0.28 ng/mL for the 4 mg naloxone strength Suboxone® (Suboxone® Tablet 2018 Patient Package Insert).

The 6 mg naloxone composition described in the Examples below, when administered sublingually, had peak naloxone levels of 2.6 ng/mL, or 3.7 times greater when dose adjusted to the 4 mg naloxone strength Suboxone® SLT. This pharmacokinetic (PK) data substantiated that this novel drug delivery technology significantly increases naloxone's bioavailability over Suboxone®.

In certain embodiments, the present invention provides, inter alia, processes for preparing rapid onset transmucosal naloxone delivery systems (or isomers or derivatives thereof).

Compounding the liquid, gel, or semi-solid formulation, according to embodiments of the present invention, includes forming a homogeneous solution of naloxone base and a solvent vehicle including one or more non-aqueous solvents, in which naloxone is a completely dissolved solute. In certain embodiments, the liquid, gel, or semi-solid formulation may further include one or more viscosity adjusting agents. Without being bound by theory, increasing the drug vehicle viscosity increases the residence time in the oral cavity and thereby minimizes the amount of naloxone that will be swallowed. For clarification, naloxone base is completed dissolved in this non-aqueous solvent system or vehicle to form a true single-phase solution. As such, this vehicle composition does not include emulsifiers or surfactants, which would result in two-phase systems such as an emulsion, dispersion, or liquid crystalline systems or precursors to such systems, e.g., self-emulsifying drug delivery systems.

In embodiments of the present invention, the non-aqueous solvent system including one or more non-aqueous solvents may include one or more solvents selected from the group consisting of oleic acid, polyethylene glycol, propylene glycol, ethanol, or mixtures thereof. Polyethylene glycols that are liquids under ambient conditions may be used as solvents in the non-aqueous solvent systems of embodiments of the present invention and may be selected from the group consisting of PEGs having a molecular weight of 600 or less, e.g., PEG 200, PEG 300, PEG 400, and PEG 600.

As described herein, the formulations comprise one or more non-aqueous solvents and are therefore substantially free of water; however, the formulations may comprise a small amount of water, such as incidental water content due to absorption of water from the environment, including from use of excipients that contain an incidental amount of water. For example, some commercially available PEGs may contain up to about 2% water.

In certain embodiments of the present invention, the liquid, gel, or semi-solid formulations may include one or more viscosity adjusting agents selected from the group consisting of calcium silicate, acacia, carbomers, carboxymethylcellulose sodium, silicon dioxide, hydroxyethyl cellulose, hydroxyethylmethyl cellulose, hydroxypropyl cellulose, hypromellose, methylcellulose, polyvinylpyrrolidone, polyvinyl alcohol, polyethylene glycol or mixtures thereof. Polyethylene glycols that are solids under ambient conditions may be used as viscosity adjusting agents in the non-aqueous solvent vehicle of embodiments of the present invention, and may be selected from the group consisting of PEGs having a molecular weight of greater than 600, e.g., PEG 1000, 1500, 2000. Although one or more viscosity adjusting agents are within the purview of the present invention any functionally equivalent to one or more viscosity adjusting agents selected from the group consisting of calcium silicate, acacia, carbomers, carboxymethylcellulose sodium, silicon dioxide, hydroxyethyl cellulose, hydroxyethylmethyl cellulose, hydroxypropyl cellulose, hypromellose, methylcellulose, polyvinylpyrrolidone, polyvinyl alcohol, polyethylene glycol, and mixtures thereof.

In one embodiment, the present invention is directed to liquid, gel, or semi-solid formulations including an effective amount of naloxone base, or isomer or derivative thereof, and a non-aqueous solvent system including one or more non-aqueous solvents.

In another embodiment, the present invention is directed to liquid, gel, or semi-solid formulations including an effective amount of naloxone base, or isomer or derivative thereof, a non-aqueous solvent system including one or more non-aqueous solvents, and one or more viscosity adjusting agents.

In various embodiments, the present invention is directed to a liquid, gel, or semi-solid formulation including: naloxone base, or an isomer or derivative thereof, in an amount of from about 1% to about 25% of the total mass of the formulation; and one or more non-aqueous solvents in a collective amount of from about 50% to about 99% of the total mass of the formulation. Optionally, the formulation may further comprise from about 1% to about 25% of one or more viscosity adjusting agents.

In various embodiments, the formulation comprises from about 1% to about 15% or from about 1% to about 10% of naloxone base, by the total mass of the formulation. In various embodiments, the formulation comprises a collective amount of from about 60% to about 99%, from about 70% to about 99%, or from about 75% to about 99% of one or more non-aqueous solvents, by the total mass of the formulation. In other various embodiments, the formulation comprises a collective amount of from about 50% to about 98%, from about 60% to about 98%, from about 70% to about 98%, or from about 75% to about 98% of one or more non-aqueous solvents, by the total mass of the formulation. And in yet other various embodiments, the formulation comprises a collective amount of from about 50% to about 90%, from about 60% to about 90%, from about 70% to about 90%, or from about 75% to about 90% of one or more non-aqueous solvents, by the total mass of the formulation. In various embodiments, the formulation comprises from about 9% to about 25% or from about 9% to about 20% of the one or more viscosity adjusting agents, by the total mass of the formulation.

In a preferred embodiment of the liquid, gel, or semi-solid formulation, the one or more non-aqueous solvents are selected from the group consisting of oleic acid and ethanol. In another preferred embodiment of the liquid, gel, or semi-solid formulation, the formulation includes oleic acid in an amount of from about 70% to about 95% of the total mass of the formulation. In yet another preferred embodiment of the liquid, gel, or semi-solid formulation, the formulation includes ethanol in an amount of from about 0.01% to about 30% of the total mass of the formulation. In one embodiment, the formulation includes naloxone base, or an isomer or derivative thereof, in an amount from about 1% to about 15% of the total mass of the formulation. In one embodiment, the formulation includes naloxone base, or an isomer or derivative thereof, in an amount from about 2% to about 10% of the total mass of the formulation.

In another embodiment, the present invention is directed to a liquid, gel, or semi-solid formulation including: naloxone base, or a derivative thereof, in an amount of from about 1% to about 30% of the total mass of the formulation; one or more non-aqueous solvents in a collective amount of from about 65% to about 98% of the total mass of the formulation; and optionally one or more viscosity adjusting agents in a collective amount of from about 1% to about 20% of the total mass of the formulation.

In one preferred embodiment of the liquid, gel, or semi-solid formulation, the one or more non-aqueous solvents are selected from the group consisting of oleic acid and ethanol and a combination thereof. In another preferred embodiment of the liquid, gel, or semi-solid formulation, the formulation includes oleic acid in an amount of from about 60% to about 90% of the total mass of the formulation. In yet another preferred embodiment of the liquid, gel, or semi-solid formulation, the formulation includes ethanol in an amount of from about 5% to about 30% of the total mass of the formulation. In another embodiment of the liquid, gel, or semi-solid formulation, the one or more viscosity adjusting agents is silicon dioxide. In yet another embodiment of the liquid, gel, or semi-solid formulation, the formulation includes silicon dioxide in an amount of from about 1% to about 25% of the total mass of the formulation.

In another preferred embodiment of the liquid, gel, or semi-solid formulation, the one or more non-aqueous solvents are selected from the group consisting of polyethylene glycol, propylene glycol, ethanol, and any combination thereof. In another preferred embodiment of the liquid, gel, or semi-solid formulation, the formulation includes polyethylene glycol in an amount of from about 60% to about 99% of the total mass of the formulation. In yet another preferred embodiment of the liquid, gel, or semi-solid formulation, the formulation includes propylene glycol in an amount of from about 5% to about 20% of the total mass of the formulation. In yet another preferred embodiment of the liquid, gel, or semi-solid formulation, the formulation includes ethanol in an amount of from about 5% to about 25% of the total mass of the formulation. In another embodiment of the liquid, gel, or semi-solid formulation, the one or more viscosity adjusting agents is silicon dioxide. In yet another embodiment of the liquid, gel, or semi-solid formulation, the formulation includes silicon dioxide in an amount of from about 1% to about 25% of the total mass of the formulation.

In another embodiment, the liquid, gel, or semi-solid formulation comprises from about 1% to about 25% of naloxone base, and from about 60% to about 99% polyethylene glycol, and optionally from about 5% to about 20% propylene glycol, and optionally from about 5% to about 25% ethanol.

In some embodiments, the formulation is a liquid formulation. In other embodiments, the formulation is a gel formulation. And in yet other embodiments, the formulation is a semisolid formulation.

In some embodiments, the liquid, gel, or semi-solid formulations described herein consist of, or consist essentially of, the components described. For example, in some embodiments the liquid, gel, or semi-solid formulations consist of, or consist essentially of: naloxone base, or isomer or derivative thereof, in an amount of from about 1% to about 25% of the total mass of the formulation; and one or more non-aqueous solvents in a collective amount of from about 50% to about 99% of the total mass of the formulation; and optionally from about 1% to about 25% of one or more viscosity adjusting agents.

In embodiments of the present invention, the liquid, gel, or semi-solid formulation may be packaged in such manner as to aid in maintaining stability of the formulation in a single-unit dose dispenser. Packaging methods and materials may include, but are not limited to, spray dispensers, oral syringes, blow-fill-seal ("BFS") unit-dose dispensers, and other dosage form containers suitable for direct administration of the liquid, gel, or semi-solid formulations of the present invention to the oral or nasal mucosa. The packaging methods and materials for the liquid, gel, or semi-solid formulations of the present invention employ manufacturing techniques familiar to one versed in the art of formulating and processing pharmaceutical dosage forms.

In embodiments of the present invention, a rapid, bolus, transmucosal dose of naloxone base is provided that is formulated as a liquid, gel, or semi-solid. In certain embodiments, the rapid, bolus, transmucosal dosage form releases naloxone relatively quickly, resulting in transmucosal absorption of naloxone in less than about 30 minutes. In other embodiments, transmucosal absorption of naloxone occurs in less than about 15 minutes. In other embodiments, transmucosal absorption of naloxone occurs in less than about 12.5 minutes. In other embodiments, transmucosal absorption of naloxone occurs in less than about 10 minutes. In other embodiments, transmucosal absorption of naloxone occurs in less than about 7.5 minutes. In other embodiments, transmucosal absorption of naloxone occurs in less than about 5 minutes. In other embodiments, transmucosal absorption of naloxone occurs in less than about 4 minutes. In other embodiments, transmucosal absorption of naloxone occurs in less than about 3 minutes. In other embodiments, transmucosal absorption of naloxone occurs in less than about 2.5 minutes. In other embodiments, transmucosal absorption of naloxone occurs in less than about 2 minutes. In other embodiments, transmucosal absorption of naloxone occurs in less than about 1.5 minutes. In other embodiments, transmucosal absorption of naloxone occurs in less than about 1 minute. In other embodiments, transmucosal absorption of naloxone occurs in less than about 0.5 minutes.

The naloxone liquid, gel, or semi-solid formulations according to embodiments of the present invention are useful in the acute treatment of respiratory depression in an individual exhibiting symptoms associated with known or suspected opioid overdose.

In an embodiment, a method of treating respiratory depression in an individual exhibiting symptoms associated with known or suspected opioid overdose can include the steps of:

(a) providing a single dosage form of a liquid, gel, or semi-solid formulation including a solution of naloxone base, or an isomer or a derivative thereof, as a completely, homogeneously dissolved solute in a non-aqueous solvent system; and (b) administering the single dosage sublingually or buccally to the individual.

More generally, a formulation, composition or dosage described herein may be administered transmucosally to the oral, esophageal or nasal mucosa. For example, the dosage may be administered by a blow-fill-seal unit dose dispenser, oral syringe, or spray delivery.

The process described herein effects a method of treating respiratory depression in an individual exhibiting symptoms associated with known or suspected opioid overdose.

In another embodiment, a method of treating respiratory depression in an individual exhibiting symptoms associated with known or suspected opioid overdose can include the steps of:

(a) providing a single dosage form of a liquid, gel, or semi-solid formulation including a solution of naloxone base, isomer or a derivative thereof, as a completely, homogeneously and completely dissolved solute in a non-aqueous solvent system, and a viscosity adjusting agent; and (b) administering the single dosage form sublingually or buccally to the individual.

The process described herein effects a method of treating respiratory depression in an individual exhibiting symptoms associated with known or suspected opioid overdose. In yet another embodiment, a method of treating respiratory depression in an individual exhibiting symptoms associated with known or suspected opioid overdose can include the steps of:

(a) providing a single dosage form of a liquid, gel, or semi-solid formulation including a solution of naloxone base, isomer or a derivative thereof, as a completely, homogeneously dissolved solute in a non-aqueous solvent system;

(b) administering the single dosage form sublingually or buccally to the individual; and (c) repeating step (b) if the individual does not recover from respiratory depression within from about 2 to about 5 minutes following the administering of step (b).

The process described herein effects a method of treating respiratory depression in an individual exhibiting symptoms associated with known or suspected opioid overdose. In yet another embodiment, a method of treating respiratory depression in an individual exhibiting symptoms associated with known or suspected opioid overdose can include the steps of:

(a) providing a single dosage form of a liquid, gel, or semi-solid formulation including a solution of naloxone base, or an isomer or a derivative thereof, as a completely, homogeneously dissolved solute in a non-aqueous solvent system, and a viscosity adjusting agent;

(b) administering the single dosage form sublingually or buccally to the individual; and (c) repeating step (b) if the individual does not recover from respiratory depression within from about 2 to about 5 minutes following the administering of step (b).

The process described herein effects a method of treating respiratory depression in an individual exhibiting symptoms associated with known or suspected opioid overdose.

Single dosage forms of the liquid, gel, or semisolid formulations according to the embodiments of the present invention including naloxone base, or an isomer or a derivative thereof, may contain an effective amount of naloxone base, or an isomer or a derivative thereof. The effective amount of naloxone base, or derivative thereof, is sufficient to treat respiratory depression in an individual exhibiting symptoms associated with known or suspected opioid overdose. In certain embodiments of the present invention, a single dosage form may contain naloxone base, or an isomer or a derivative thereof, in an amount of about 1 mg to about 20 mg. In other embodiments of the present invention, a single dosage form may contain naloxone base, or an isomer or a derivative thereof, in an amount of about 5 mg to about 15 mg. In other embodiments of the present invention, a single dosage form may contain naloxone base, isomer or a derivative thereof, in an amount of about 10 mg. In other embodiments of the present invention, a single dosage form may contain naloxone base, isomer or a derivative thereof, in an amount of about 1 mg, about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, or about 20 mg.

In certain embodiments of the present invention, the concentration of naloxone base, or an isomer or a derivative thereof, as completely and homogenously dissolved solute in a non-aqueous solvent system, as a percentage of mass of naloxone base to total mass of solvent system, is from about 1% to about 25%. In other embodiments of the present invention, the concentration of naloxone base, or a derivative thereof, as completely and homogeneously dissolved solute in a non-aqueous solvent system, as a percentage of mass of naloxone base to total mass of solvent system, is from about 5% to about 20%. In other embodiments of the present invention, the concentration of naloxone base, or an isomer or a derivative thereof, as completely and homogeneously dissolved solute in a non-aqueous solvent system, as a percentage of mass of naloxone base to total mass of solvent system, is from about 10% to about 15%. In other embodiments of the present invention, the concentration of naloxone base, or a derivative thereof, as completely and homogeneously dissolved solute in a non-aqueous solvent system, as a percentage of mass of naloxone base to total mass of solvent system, is from about 1% to about 10%. In other embodiments of the present invention, the concentration of naloxone base, or a derivative thereof, as completely and homogeneously dissolved solute in a non-aqueous solvent system, as a percentage of mass of naloxone base to total mass of solvent system, is from about 10% to about 25%. In other embodiments of the present invention, the concentration of naloxone base, or a derivative thereof, as completely and homogeneously dissolved solute in a non-aqueous solvent system, as a percentage of mass of naloxone base to total mass of solvent system, is about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, or about 25%.

The term "recover," as used herein, alone or in combination with other terms, unless stated otherwise, means observable amelioration of physical symptoms conventionally associated with respiratory depression, including, but not limited to, reversal of respiratory depression.

The term "effective amount," as used herein, alone or in combination with other terms, means an amount necessary to treat an individual in need thereof.

Derivatives of naloxone that can be used in accordance with embodiments of the present invention include, but are not limited to: 3-O-acyl, phenylhydrazone, and methiodide derivatives of naloxone.

3-O-Acyl derivatives of naloxone have the following general chemical structure:

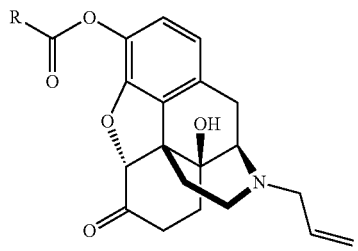

3-O-Acyl Derivatives of Naloxone wherein R is selected from the group consisting of $(C_1-C_{15})$ alkyl, $(C_2-C_{15})$alkenyl, and $(C_2-C_{15})$ alkynyl.

The phenylhydrazone derivative of naloxone has the following chemical structure:

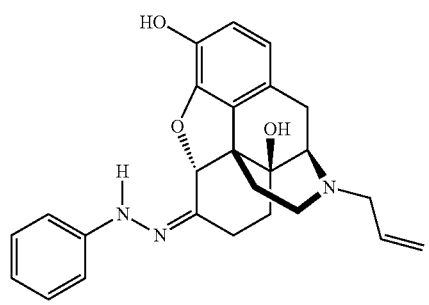

Phenylhydrazone Derivative of Naloxone

The methiodide derivative of naloxone has the following chemical structure:

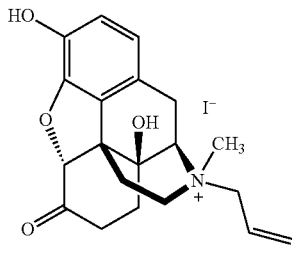

Methiodide Derivative of Naloxone

It will be readily understood that the compositions, ingredients, solvents, agents, formulations, processes, and methods of the present invention, as generally described herein, are arranged and designed in a wide variety of dosage forms and formulations. The compositions, ingredients, solvents, agents, formulations, processes, and methods described herein in the embodiments above may be further understood in connection with the following Examples. In addition, the following non-limiting Examples are intended to illustrate the invention. However, the person skilled in the art will appreciate that it may be necessary to vary the procedures for any given embodiment of the invention, e.g., vary the order or steps of the methods and/or the compositions, ingredients, solvents, agents, and/or formulations used.

Example 1A

In an embodiment, the present invention provides a liquid solution dosage form composition, having a total mass of about 62.6 milligrams ("mg"), including 6 mg of naloxone base, oleic acid, and ethanol. In such an embodiment, naloxone is mixed with oleic acid and ethanol until the naloxone is completely dissolved in the oleic acid and ethanol so as to form a homogeneous solution. An exemplary formulation in accordance with this embodiment includes mass amounts of ingredients according to Table 1A, below.

TABLE 1A

| 6 mg Naloxone Liquid Solution Dosage Form Composition ||
|---|---|
| Ingredient | Mass Amount (mg/dose) |
| Naloxone Base | 6.0 |
| Oleic acid | 51.0 |
| Ethanol | 5.6 |
| Total Mass (mg) | 62.6 |

Example 1B 6 mg Naloxone Liquid Solution Dosage Form Composition

In an embodiment, the present invention provides a viscous liquid solution dosage form composition, having a total mass of about 72.6 milligrams ("mg"), including 6.0 mg of naloxone base, oleic acid, ethanol and silicon dioxide. An exemplary formulation in accordance with this embodiment includes mass amounts of ingredients according to Table 1B, below.

TABLE 1B 6 mg Naloxone Liquid Solution Dosage Form Composition

| Ingredient | Mass Amount (mg/dose) |
|---|---|
| Naloxone Base | 6.0 |
| Oleic acid | 51.0 |
| Ethanol | 5.6 |
| Silicon Dioxide | 10.0 |
| Total Mass (mg) | 72.6 |

Example 2

10 mg Naloxone Liquid Solution Dosage Form Composition

In an embodiment, the present invention provides a liquid solution dosage form composition, having a total mass of about 250 mg, including 10 mg of naloxone base, and polyethylene glycol 300. In such an embodiment, naloxone is mixed with polyethylene glycol 300 until the naloxone is completely dissolved in the polyethylene glycol 300 so as to form a homogeneous solution. An exemplary formulation in accordance with this embodiment includes mass amounts of ingredients according to Table 2, below.

TABLE 2

| Ingredient | Mass Amount (mg/dose) |
|---|---|
| Naloxone Base | 10.0 |
| Polyethylene glycol 300 | 240.0 |
| Total Mass (mg) | 250.0 |

Example 3A 10 mg Naloxone Liquid Solution Dosage Form Composition

In an embodiment, the present invention provides a liquid solution dosage form composition, having a total mass of about 126 mg, including 10 mg of naloxone base, polyethylene glycol 300, propylene glycol, and ethanol. In such an embodiment, naloxone is mixed with polyethylene glycol 300, propylene glycol, and ethanol until the naloxone is completely dissolved in the polyethylene glycol 300, propylene glycol, and ethanol so as to form a homogeneous solution. An exemplary formulation in accordance with this embodiment includes mass amounts of ingredients according to Table 3A, below.

TABLE 3A

| Ingredient | Mass Amount (mg/dose) |
|---|---|
| Naloxone Base | 10.0 |
| Polyethylene glycol 300 | 90.0 |
| Propylene glycol | 10.8 |
| Ethanol | 15.2 |
| Total Mass (mg) | 126.0 |

Example 3B 10 mg Naloxone Liquid Solution Dosage Form Composition

In an embodiment, the present invention provides a viscous liquid solution dosage form composition, having a total mass of about 145 mg, including 10 mg of naloxone base, polyethylene glycol 300, propylene glycol, ethanol, and silicon dioxide. An exemplary formulation in accordance with this embodiment includes mass amounts of ingredients according to Table 3B, below.

TABLE 3B

| Ingredient | Mass Amount (mg/dose) |
|---|---|
| Naloxone Base | 10.0 |
| Polyethylene glycol 300 | 90.0 |
| Propylene glycol | 10.8 |
| Ethanol | 15.2 |
| Silicon Dioxide | 19.0 |
| Total Mass (mg) | 145.0 |

Example 4

The pharmacokinetics of a naloxone 6 mg composition of Example 1B was investigated when administered sublingually. The plasma concentration of naloxone following administration are presented in FIG. 1. The intramuscular ("IM") and 6 mg composition demonstrated lag times (i.e., the time needed to exceed 0.5 ng/mL) of between 5 and 10 minutes. The 6 mg dose showed greater naloxone plasma concentration levels at 15 minutes compared to that of the intramuscular (i.e., 0.92 ng/mL and 0.70 ng/mL, respectively). The $C_{max}$ was greater for sublingual administration, being 2.6 ng/mL vs. 0.75 ng/mL for the IM. Thus, transmucosal absorption of 6 mg composition from administration sublingually exceeded the 0.4 mg IM administration drug exposure. The pharmacokinetics of a naloxone 10 mg composition of Example 3B were investigated when administered both sublingually and on top of the tongue. The plasma concentration of naloxone following administration of the 10 mg composition sublingually and on the top of the tongue are presented in FIG. 1. The intramuscular ("IM") and both 10 mg compositions demonstrated lag times (i.e., the time needed to exceed 0.5 ng/mL) of between 5 and 10 minutes. Both 10 mg administrations showed greater naloxone plasma concentration levels at 10 minutes compared to that of the intramuscular, i.e. 2.5 ng/mL (sublingual), 0.94 ng/mL (on tongue), and 0.58 ng/mL, respectively). The $C_{max}$ was greater for administration on top of the tongue, 5.2 ng/mL, vs. 3.9 ng/mL sublingually. The absorption of naloxone took a few more minutes on top of the tongue; however, the maximum plasma concentration of naloxone achieved was greater than for administration sublingually and for intranasal ("IN") spray. Without being bound by theory, these results may be explained by mucosal physiology. The sublingual mucosa is thin (~100 μm), not keratinized, and has a lower surface area, while the mucosa of the tongue is thicker (~200 μm), keratinized, and has a greater surface area due to papillae. Thus, transmucosal absorption from administration either sublingually or on top of the tongue provides comparable drug exposure and exceeds the 0.4 mg IM administration drug exposure.

Pharmacokinetic data from the naloxone 6 mg and 10 mg compositions also demonstrated greater exposure compared to the 0.4 mg IM injection, thereby exceeding the Reference Listed Drug ("RLD") standard. The 6 mg strength peak naloxone plasma concentration levels were 3.5 times greater than that of the IM injection and 5 to 7 times greater for the 10 mg strength. The IM and IN pharmacokinetic data used for this comparison were obtained from Narcan® IN spray Clinical Pharmacology Review in 29 subjects. A graph of naloxone plasma concentration levels comparing a 6 mg composition (n=1) to the 0.4 mg IM injection and 4 mg IN spray with 90% CI is depicted in FIG. 1. Naloxone plasma concentration levels beyond the 10-minute time point substantially exceeded the IM plasma concentration levels and the 10 mg strength was comparable to the IN spray plasma concentration levels.

The plasma curve for the 10 mg compositions from sublingual administration is similar to that of the IN spray. The lag time is several minutes longer for the sublingual administration; however, both curves reached 1.5 ng/mL naloxone plasma concentration levels within 2 minutes of the other (i.e., 7 minutes for the 10 mg composition vs. 5 minutes for the intranasal spray). Similarly, the 2.5 ng/mL plasma concentration level is reached at 10 minutes for sublingual administration vs. 8 minutes for the intranasal spray. Both the 6 mg and 10 mg compositions and the IN spray reach $T_{max}$ at 20 minutes. The IN spray has a slightly higher $C_{max}$ of 4.5 ng/mL compared to 3.9 ng/mL for the 10 mg composition administered sublingually. Prior pharmacokinetic studies with similar formulations have shown good correlation between dose and $C_{max}$. Therefore, a higher $C_{max}$ may be expected by increasing the dose of naloxone, should that be deemed desirable.

The use of the terms "a," "an," "the," and similar referents in the context of describing the presently claimed invention (especially in the context of the claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. Use of the term "about" is intended to describe values either above or below the stated value in a range of approximately ±10%; in other embodiments the values may range in value either above or below the stated value in a range of approximately ±5%; in other embodiments the values may range in value either above or below the stated value in a range of approximately ±2%; in other embodiments the values may range in value either above or below the stated value in a range of approximately ±1%. The preceding ranges are intended to be made clear by context, and no further limitation is implied. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

While in the foregoing specification this invention has been described in relation to certain embodiments thereof, and many details have been put forth for the purpose of illustration, it will be apparent to those skilled in the art that the invention is susceptible to additional embodiments and that certain of the details described herein can be varied considerably without departing from the basic principles of the invention.

All references cited herein are incorporated by reference in their entireties. The present invention may be embodied in other specific forms without departing form the spirit or essential attributes thereof and, accordingly, reference should be made to the appended claims, rather than to the foregoing specification, as indicating the scope of the invention.

What is claimed is:

1. A method for treating an individual exhibiting symptoms of respiratory depression associated with known or suspected opioid overdose comprising
   administering a pharmaceutical composition sublingually or buccally to the individual, wherein the pharmaceutical composition is a liquid, gel or semi-solid pharmaceutical composition comprising from about 1% to about 25% of naloxone base, or an isomer or a derivative thereof, by the total mass of the composition; and from about 50% to about 99% of one or more non-aqueous solvents selected from the group consisting of oleic acid, liquid polyethylene glycol, propylene glycol, and ethanol, or mixtures thereof, by the total mass of the composition; wherein the composition is substantially free of water; and wherein the naloxone base, or isomer or derivative thereof, is completely and homogeneously dissolved in the one or more non-aqueous solvents.

2. The method of claim 1, wherein the pharmaceutical composition further comprises one or more viscosity adjusting agents.

3. The method of claim 2, wherein the one or more viscosity adjusting agents are selected from the group consisting of calcium silicate, acacia, carbomers, carboxymethylcellulose sodium, silicon dioxide, hydroxyethyl cellulose, hydroxyethylmethyl cellulose, hydroxypropyl cellulose, hypromellose, methylcellulose, polyvinylpyrrolidone, polyvinyl alcohol, polyethylene glycol or mixtures thereof, by the total mass of the composition.

4. The method of claim 1, further comprising
   repeating administration of the pharmaceutical composition if the individual does not recover from respiratory depression within from about 2 to about 5 minutes following administration.

5. The method of claim 1, wherein the plasma concentration of naloxone in the individual is at least about 1 ng/mL in less than about 10 minutes following administration.

6. The method of claim 1, wherein the pharmaceutical composition is a liquid pharmaceutical composition.

7. The method of claim 1, wherein the pharmaceutical composition is administered from a single unit dosage form container selected from the group consisting of a spray dispenser, an oral syringe, or a blow-fill-seal unit dose dispenser.

* * * * *